(12) United States Patent
French et al.

(10) Patent No.: US 7,354,396 B2
(45) Date of Patent: Apr. 8, 2008

(54) PASSIVE VENTRICULAR SUPPORT DEVICES AND METHODS OF USING THEM

(75) Inventors: Ronald G. French, Santa Clara, CA (US); Sunmi K. Chew, San Jose, CA (US); Hanson S. Gifford, III, Woodside, CA (US); Bernard H. Andreas, Redwood City, CA (US)

(73) Assignee: The Foundry, Inc., Menlo Park, CA (US)

( * ) Notice: Subject to any disclaimer, the term of this patent is extended or adjusted under 35 U.S.C. 154(b) by 705 days.

(21) Appl. No.: 10/715,650

(22) Filed: Nov. 17, 2003

(65) Prior Publication Data

US 2004/0097787 A1 May 20, 2004

Related U.S. Application Data

(63) Continuation of application No. 09/963,921, filed on Sep. 25, 2001, now Pat. No. 6,695,769.

(51) Int. Cl.
*A61F 2/00* (2006.01)
(52) U.S. Cl. ........................................ 600/37
(58) Field of Classification Search ............ 600/16–18, 600/37; 128/897–899; 623/3.1, 3.11, 3.29
See application file for complete search history.

(56) References Cited

U.S. PATENT DOCUMENTS

| | | | |
|---|---|---|---|
| 2,826,193 A | 3/1958 | Vineberg | |
| 3,464,322 A | 9/1969 | Pequignot | |
| 3,513,836 A | 5/1970 | Sausse | |
| 3,587,567 A | 6/1971 | Schiff | |
| 3,613,672 A | 10/1971 | Schiff | |
| 3,983,863 A | 10/1976 | Janke et al. | |
| 4,536,893 A | 8/1985 | Parravicini | |
| 4,628,937 A | 12/1986 | Hess et al. | |

(Continued)

FOREIGN PATENT DOCUMENTS

EP    0 370 931 A1    5/1990

(Continued)

OTHER PUBLICATIONS

Athanasuleas, C. et al., (2001). "Surgical Anterior Ventricular Endocardial Restoration (SAVER) in the Dilated Remodeled Ventricle After Anterior Myocardial Infarction," *JACC* 37(5):1199-1209.

(Continued)

*Primary Examiner*—Samuel G Gilbert
(74) *Attorney, Agent, or Firm*—Townsend and Townsend and Crew LLP (57) ABSTRACT

A device for supporting or constraining at least some part of the epicardial surface of the heart during a portion of the heartbeat, such as diastole is used to assist in the treatment of congestive heart failure. The device comprises an enclosure having an interior and an exterior. An interior surface is preferably made in such a way that it tends not to or does not form adhesions with or accept ingrowth with the myocardial tissue of the epicardium. The device may comprise at least on rib-like structural member.

19 Claims, 13 Drawing Sheets

U.S. PATENT DOCUMENTS

| | | | |
|---|---|---|---|
| 4,690,134 A | 9/1987 | Snyders | |
| 4,827,932 A | 5/1989 | Ideker et al. | |
| 4,936,857 A * | 6/1990 | Kulik | 623/3.1 |
| 4,957,477 A | 9/1990 | Lundbäck | |
| 4,972,300 A | 11/1990 | Beisswanger et al. | |
| 4,973,300 A | 11/1990 | Wright | |
| 5,098,369 A | 3/1992 | Heilman et al. | |
| 5,119,804 A | 6/1992 | Anstadt | |
| 5,131,905 A | 7/1992 | Grooters | |
| 5,256,132 A | 10/1993 | Snyders | |
| 5,336,252 A * | 8/1994 | Cohen | 607/119 |
| 5,336,254 A | 8/1994 | Brennen et al. | |
| 5,383,840 A | 1/1995 | Heilman et al. | |
| 5,603,337 A | 2/1997 | Jarvik | |
| 5,643,172 A | 7/1997 | Kung et al. | |
| 5,702,343 A | 12/1997 | Alferness | |
| 5,707,336 A | 1/1998 | Rubin | |
| 5,713,954 A | 2/1998 | Rosenberg et al. | |
| 5,800,528 A | 9/1998 | Lederman et al. | |
| 5,900,528 A | 5/1999 | Bergquist | |
| 5,961,440 A | 10/1999 | Schweich, Jr. et al. | |
| 6,037,366 A | 3/2000 | Krall et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,076,013 A | 6/2000 | Brennan et al. | |
| 6,077,214 A | 6/2000 | Mortier et al. | |
| 6,077,218 A | 6/2000 | Alferness | |
| 6,085,754 A | 7/2000 | Alferness et al. | |
| 6,095,968 A * | 8/2000 | Snyders | 600/16 |
| 6,109,972 A | 8/2000 | Leinonen et al. | |
| 6,110,100 A | 8/2000 | Talpade | |
| 6,123,662 A | 9/2000 | Alferness et al. | |
| 6,126,590 A | 10/2000 | Alfereness | |
| 6,155,972 A | 12/2000 | Nauertz et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,165,121 A * | 12/2000 | Alferness | 600/37 |
| 6,165,122 A | 12/2000 | Alferness | |
| 6,169,922 B1 | 1/2001 | Alferness et al. | |
| 6,174,279 B1 | 1/2001 | Girard | |
| 6,183,411 B1 | 2/2001 | Mortier et al. | |
| 6,190,408 B1 | 2/2001 | Melvin | |
| 6,193,648 B1 | 2/2001 | Krueger | |
| 6,210,432 B1 | 4/2001 | Solem et al. | |
| 6,224,540 B1 | 5/2001 | Lederman et al. | |
| 6,230,714 B1 | 5/2001 | Alferness et al. | |
| 6,231,602 B1 | 5/2001 | Carpentier et al. | |
| 6,234,960 B1 | 5/2001 | Aboul-Hosn et al. | |
| 6,237,607 B1 | 5/2001 | Vanney et al. | |
| 6,241,654 B1 * | 6/2001 | Alferness | 600/37 |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,264,645 B1 | 7/2001 | Jonkman | |
| 6,293,906 B1 | 9/2001 | Vanden Hoek et al. | |
| 6,425,856 B1 | 7/2002 | Shapland et al. | |
| 6,695,769 B2 * | 2/2004 | French et al. | 600/37 |
| 6,887,192 B1 * | 5/2005 | Whayne et al. | 600/16 |

FOREIGN PATENT DOCUMENTS

| | | |
|---|---|---|
| FR | 2 645 739 | 10/1990 |
| GB | 2 115 287 A | 9/1983 |
| JP | 2-271829 | 11/1990 |
| SU | 1009457 A | 4/1983 |
| SU | 1734767 A1 | 5/1993 |
| WO | WO 00/44287 A1 | 8/2000 |
| WO | WO 01/21098 | 3/2001 |
| WO | WO 01/67985 | 9/2001 |
| WO | WO 02/28450 A2 | 4/2002 |

OTHER PUBLICATIONS

Comedicus, Inc. The PerDucer™ Brand Pericardiocentesis Device at <<http://www.comedicus.com/index.cfm>> visited on Dec. 3, 2001, 4 pages.

Mussivand, T. (1999). "Mechanical Circulatory Devices for the Treatment of Heart Failure," *J. Card. Surg.* vol. 13:218-228.

Somanetics Press Release (Apr. 4, 2001) "Journal of the American College of Cardiology Study Highlights SAVR, A Congestive Heart Failure Treatment" at <<http://www.somanetics.com/April42001.htm>>, 2 pages.

Somanectics Press Release (May 7, 2001) "13-Center SAVR Study Results Presented to Thoracic Surgeons" at <<http://www.somanectics.com/May72001.htm>>, 2 pages.

* cited by examiner

PASSIVE VENTRICULAR SUPPORT DEVICES AND METHODS OF USING THEM

CROSS-REFERENCES TO RELATED APPLICATIONS

The present application is a continuation of U.S. patent application Ser. No. 09/963,921, filed Sep. 25, 2001, the full disclosure of which is incorporated herein by reference.

BACKGROUND OF THE INVENTION

1. Field of the Invention

This invention is a surgical device and a method of using it. In particular, the device is one for supporting or constraining at least some part of the epicardial surface of the heart during a portion of the heartbeat, in particular during the diastolic cycle. This device may be used to assist in the treatment of congestive heart failure. The device, generically, is an enclosure having an interior and an exterior. The interior surface is preferably made in such a way that it tends not to form or does not form adhesions with or accept ingrowth with the myocardial tissue of the epicardium, The device preferably has at least one rib-like structural member extending for a length of the device. The rib component may extend from end-to-end or preferably extends helically around the heart, generally with at least one revolution. The device may be configured to be self-adherent, i.e., adherent only to itself, and to form after implantation, a unitary support in the pericardial space. This device helps to prevent further declination of the heart during congestive heart failure. The device is preferably introduced into the pericardial space and onto the surface of the epicardium using transcutaneous or minimally invasive techniques.

Congestive Heart Failure ("CHF"), or simply "Heart Failure" is a progressive path found in many forms of heart disease. In general, it is a condition in which the heart is unable to pump blood at a rate sufficient for the supply of nutrients to metabolizing tissues. There are many specific disease states leading to CHF, but each typically results in the dilatation of the ventricles. Various etiologies for CHF are viral and ischemic and, of course, idiopathic. Variously, myocardial injury or chronic volume overload generally are thought to cause this course of ventricular dilatation. The typical adaptation process undertaken by the stressed heart muscle is not achieved during CHF and, instead of gaining a stronger heart muscle, the heart instead gets larger as it attempts to adapt to its increased volume load.

Chronic pressure overload causes another response mechanism to develop. Specifically, hypertrophy of the heart muscle, entailing an increase both in the size of individual muscle cells and in overall muscle mass, begins to occur. Although this response helps the heart to overcome higher pressure, it has limitations and is associated with various structural and biochemical changes that have deleterious long term effects.

Additionally, system-wide vascular constriction occurs during the course of CHF. The constriction causes blood flow to be redistributed so that certain regions and systems have a reduced blood supply, e.g., skeletal muscle, kidneys, and skin. These regions do not produce significant amounts of vasodilating metabolites. In contrast, the brain and heart have high metabolic rates and produce a greater amount of vasodilators. Consequently, the latter organs receive a higher proportion of the restricted blood supply.

Therapy for CHF is staged. Correction of reversible causative factors is the first line of offense. Treatment of bradyarrhythmias, perhaps by use of an artificial pacemaker or by provision of an appropriate drug such as digitalis, can help alleviate CHF. CHF that continues after correction of such reversible causes is often treated with a regime of salt restriction, vasodilators, diuretics, and the like. Bed rest to increase venous return to the heart and move fluid from the periphery is often helpful. As noted above, digitalis has been an important drug for increasing cardiac output in persons with specific types of CHF. It has been used for over 200 years. Other drugs used for treatment of CHF include beta-adrenergic agonists such as norepinephrine, epinephrine, and isoproterenol. Each stimulate cardiac beta-adrenergic receptors. Dopamine and dobutamine are also used. Various diuretics and vasodilators for variously dilating both veins and arteries are used, each for slightly different reasons based on the detected manifestation of the CHF in the heart.

Few interventional or surgical pathways for alleviation of CHF are currently widely practiced. Indeed, the only permanent treatment for CHF is a heart transplant.

One surgical procedure known as cardiomyoplasty is used for early stage CHF. In that procedure, a muscle taken from the shoulder (the latissimus dorsi) is wrapped around the heart. The added muscle is paced synchronously with the ventricular systole. This procedure is highly invasive since it requires a sternotomy to access the heart. Some have suggested that the benefits of the procedure are due more to remodeling of the heart muscle rather than mere placement of a paced muscle around the heart.

There are a variety of devices that may be applied to the heart for treatment of CHF. U.S. patents owned by Abiomed (U.S. Pat. Nos. 6,224,540; 5,800,528; 5,643,172) generally show a girdle-like device situated to provide structure to a failing heart. U.S. patents owned by Acorn Cardiovascular, Inc. (U.S. Pat. Nos. 6,241,654; 6,230,714; 6,193,648; 6,174,279; 6,169,922; 6,165,122; 6,165,121; 6,155,972; 6,126,590; 6,123,662; 6,085,754; 6,077,218; 5,702,343) show various devices, also for treatment of CHF, that typically include a mesh sock-like device placed around the myocardial wall. U.S. patents to Myocor, Inc. (U.S. Pat. Nos. 6,264,602; 6,261,222; 6,260,552; 6,183,411; 6,165,120; 6,165,119; 6,162,168; 6,077,214; 6,059,715; 6,050,936; 6,045,497; 5,961,440) show devices for treatment of CHF generally using components that pierce the ventricular wall.

None of the documents mentioned just above describe in any way the devices and methods disclosed herein.

BRIEF SUMMARY OF THE INVENTION

This device is a passive support for constraining epicardial expansion past a predetermined limit. It generally is a flexible enclosure and conforms to the shape of at least a portion of the enclosed epicardium. Preferably, the support member is made up of at least one rib separated by and spaced by webbing. The ribs typically have a flexibility differing than the webbing flexibility. The rib members may be multiple or single, helical or longitudinal, and of a variety of cross-sections, e.g., ribbon-like (with a width-thickness ratio greater than about two, preferably greater than about seven), inflatable (perhaps incrementally inflatable), round, semicircular, or other convenient shape. The rib members may be zigzag in shape, perhaps with adjacent points that are connected. The ribs may be joined at the apical end or not. Where webbing joins the rib members, the webbing may be a woven fabric (perhaps open weave), a non-woven fabric, one or more ribbons, one or more fibers, etc. The webbing may be an elastic material or a substantially inelastic material.

The device may be a band, desirably a band having an upper end and an apical end and a length extending from the upper end to the apical end and where the length of the band is less than about ⅓ length of a heart to which it is applied, and preferably having a length substantially matching the width of the A-V groove on the heart to which it is applied.

The device may be an enclosure generally conforming in shape to at least a portion of an epicardium and having an upper end and an apical end and a length extending from the upper end to the apical end and having one or more, sometimes multiple, ribs extending from the upper end to the apical end.

The device may be a sack having a closed end, perhaps sized to be positioned along the heart from the apical end (where it is applied) and less than about ⅓ length of that heart.

Another important variation: the inventive support may be made up of at least one flexible member introducable into the pericardial space and configured to have a generally linear delivery shape but to transform into a generally helical form upon introduction into that pericardial space. The flexible member(s) may be ribbon-like members having the aspect ratios mentioned above. The ribbon-like member or members may have a flexibility and or thickness that varies along their length. The flexible member may have a lumen extending from the proximal end at least partially to the distal end and have at least one orifice situated to open to other surfaces of the generally helical member when the support is helically configured. Glue or adhesives may be passed through the lumen and the orifices. The glue may be selected so that it causes adherence only between portions of the generally helical member. The glue may comprise a modified cyanoacrylate.

DETAILED DESCRIPTION OF THE INVENTION

As noted elsewhere, this invention includes a device for supporting and constraining the epicardium during at least diastoly. The device preferably has either: 1.) a generally sack-like shape (with or without an opening at the apical end of the sack) that is adapted to fit adjacent at least a portion of the epicardial wall and has one or more ribs integral to or cooperating with the sack and most preferably where those ribs are one or more helical ribs, or 2.) at least one rib that will encircle the heart and preferably binds to itself after introduction to the vicinity of the epicardial surface. Also included are methods of introducing the inventive reinforcing device to the pericardial space.

Figure 1:
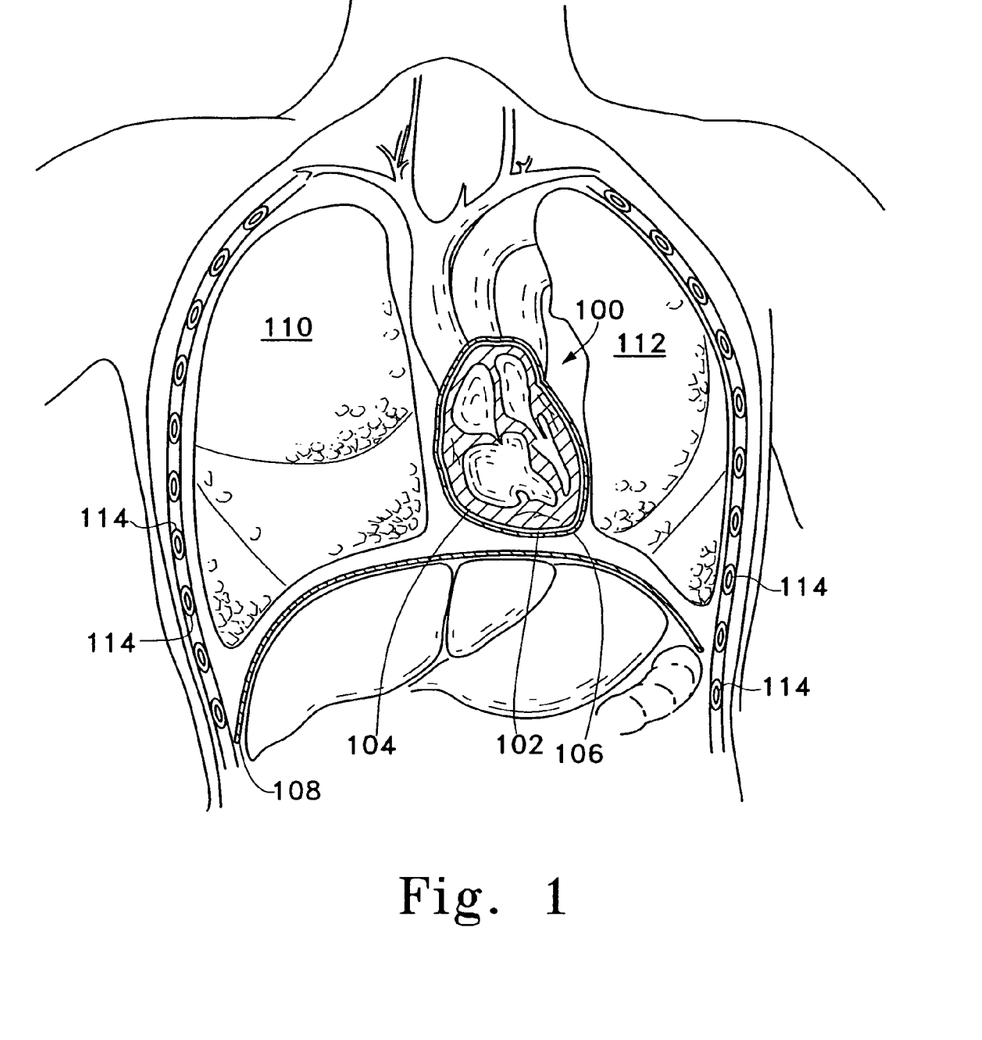
FIG. 1 is an anterior view of the heart in the human chest.

First, in FIG. 1, the placement of a typical human heart (100) in a chest may be seen. Of special interest here is the pericardial space (102) filled with a pericardial fluid surrounding the epicardium (104). The pericardial sac (106) approaches the diaphragm (108) closely at the apex or apical end of the heart. In individuals who are not obese, the distance from the exterior surface of the skin, through the diaphragm (108), and into the pericardial space (102) may be as short as a couple of inches. In obese individuals, the distance may be much greater, e.g., six inches or more. As will be discussed below, this sub-xiphoid approach (a percutaneous route as described above, but below the xiphoid process—not shown in FIG. 1) is highly desirable and even preferable to "cracking the chest" to introduce various implants into the cardiac space.

Also seen in FIG. 1 for reference are the lungs (110, 112) and the ribs (114). Note how far below the apex of the heart (100) the ribs extend.

Figure 2:
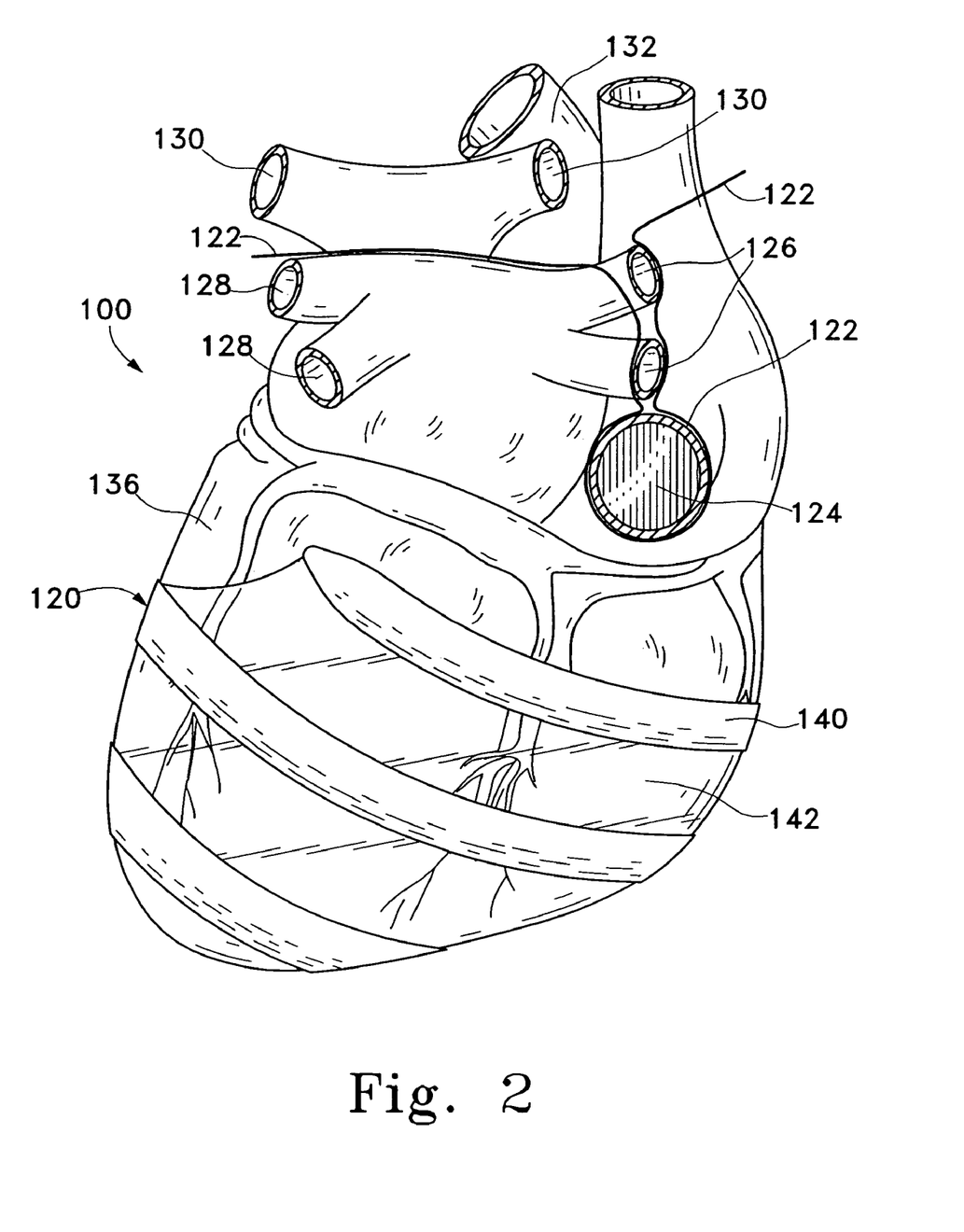
FIG. 2 is a posterior view of the heart showing placement of one variation of the inventive device.

FIG. 2 shows a posterior view of the heart (100) with a variation of the inventive device (120) installed. From this view of the heart, the pericardial reflection (122) may be seen, as well as a majority of the passageways that connect the heart to the remainder of the vascular system. The inferior vena cava, the right pulmonary veins and the left pulmonary veins (128) may be seen. The pulmonary arteries (130) and the aortic arch (132) are also visible. When the inventive device is introduced into the pericardial space (102) in FIG. 1, the upper placement of the device is defined by the pericardium and the situation of the grand veins and grand arteries. The placement of the inventive device (120) shown in FIG. 2 is for the purpose of depicting a preferred siting of the device onto the epicardial or ventricular surface (136). This variation (120) includes a helically conformed rib (140) separated and held together by at least one webbing member (142).

The inventive device provides support to the ventricular wall and further is intended to limit the radial movement of the heart wall during diastoly. By limiting the expansion of the heart, the heart will remodel to supply blood to tissues as needed by strengthening the affected muscles or by increasing the heart rate. Prior to this remodeling, there may be intermediate problems with lessening of the ejection fraction if the heart muscle is insufficiently strong to eject the normal percentage of its internal volume and allows the heart to pump blood more efficiently. The inventive device does provide a measure of benefit in this circumstance in that it limits the blood volume introduced into the chamber.

Figure 3A:
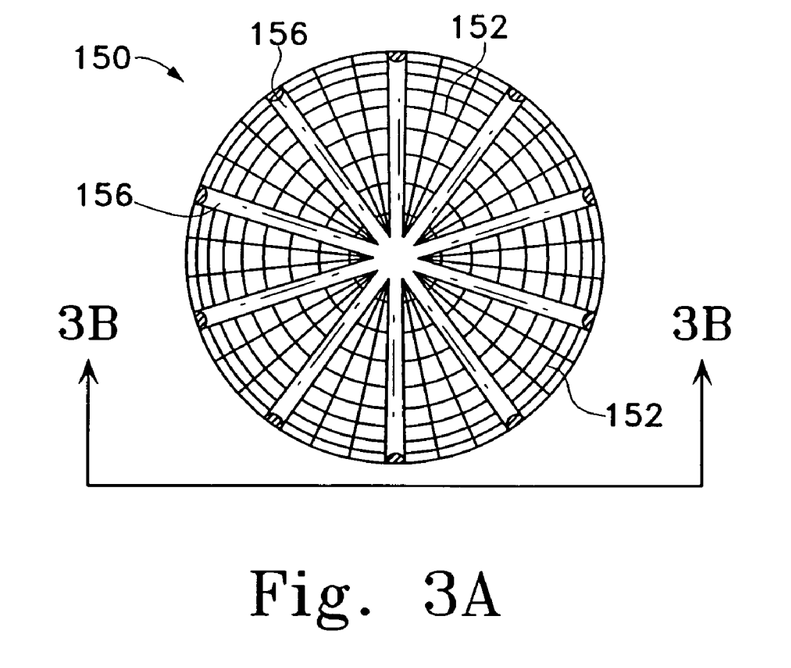
FIG. 3A shows a cross-sectional view of the compliant member making up one variation of the invention.
Figure 3B:
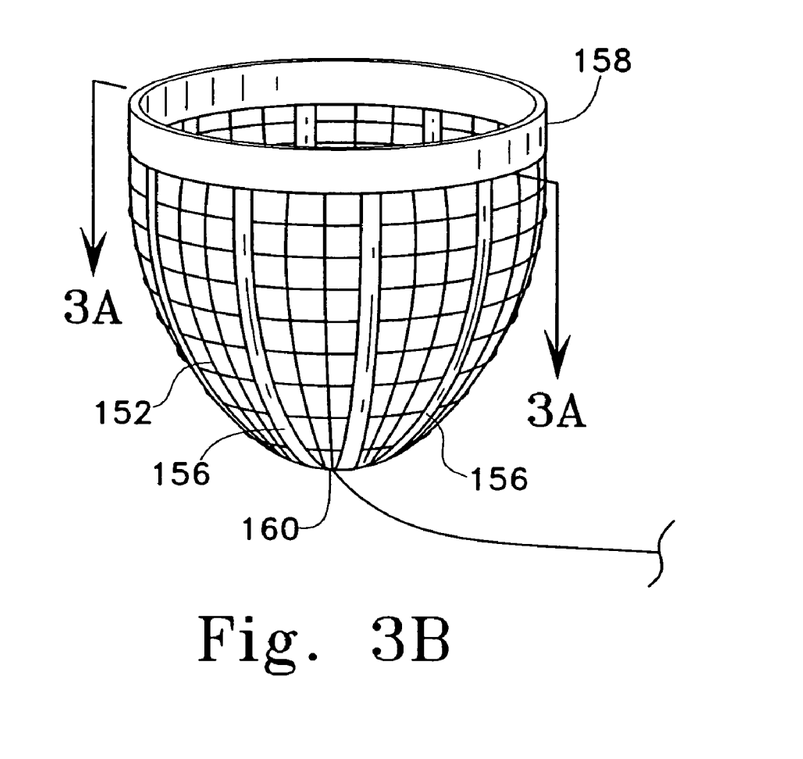
FIG. 3B shows a side-view of the FIG. 3A device.

FIGS. 3A and 3B show, respectively, a top cross-sectional view and a side view of a ribbed variation (150) of the invention. This variation (150) includes ribs (156) that extend from an upper (but optional) band (158) to an apical end (160). As may be seen in FIG. 3A, the ribs (156) may be semicircular in cross-section. Although there is a preference for the interior of the ribs (156) to be a shape conformable to the epicardium, the cross-sectional shape of the ribs is not seen to be particularly important. The ribs (156), as shown in FIGS. 3A and 3B, may stand alone but preferably are separated and held in place by webbing (152) of any of the various forms discussed herein.

Figure 4:
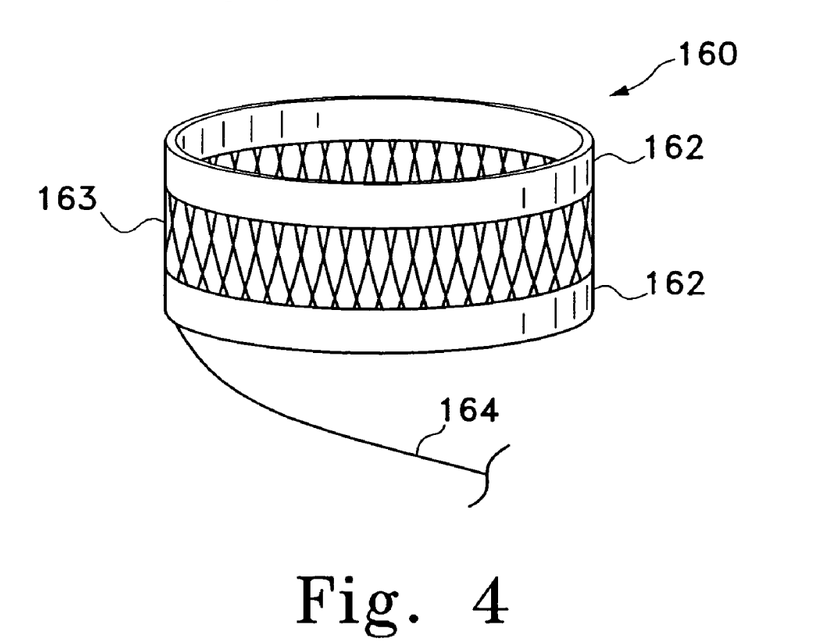
FIGS. 4 and 5 show various side-views of variations of the invention.

FIG. 4 shows a side view of a variation of the pericardial reinforcement device (160) that is open in the end normally near the apical end of the heart and generally is band-shaped. Optional upper and lower ribs or bands (162) are included. These bands (162) are to provide structure to the often more-loosely woven compliant member (163) separating them. This variation (160) is especially suitable for providing support locally to the ventricular valves, a region whose reinforcement is especially effective in alleviating congestive heart failure. This variation minimizes the mass of material implanted into the heart region, an often desirable result. A schematic introducer (164) is shown. The introducer (164) may be used to place the device into an appropriate position using the procedures discussed elsewhere.

Figure 5:
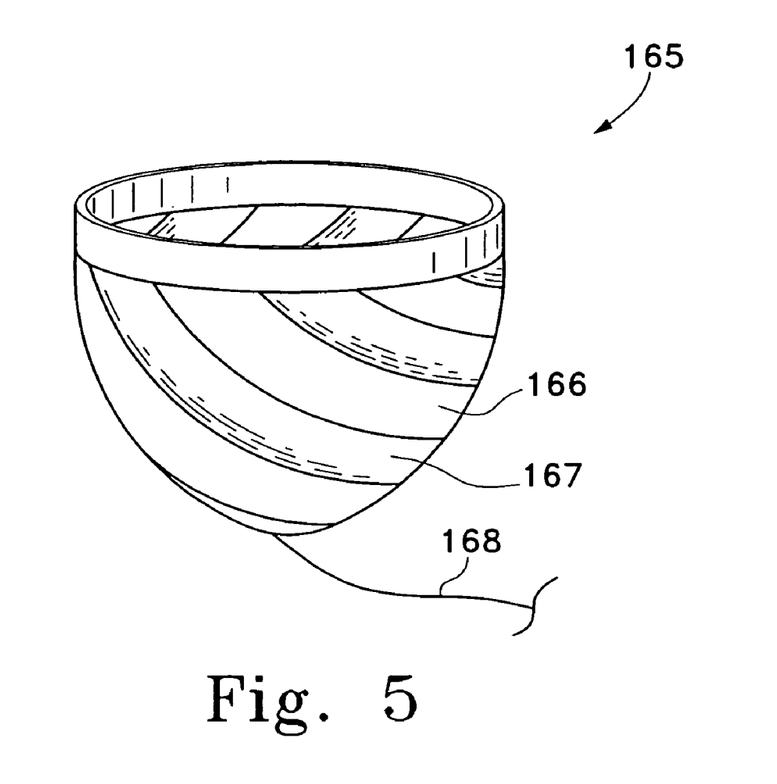

FIG. 5 shows a side view of a variation of the inventive reinforcement (165) having a generally epicardial form due to the presence of webbing (166). Webbing (166) may be fabric, individual threads, cords, etc.—many of which are discussed elsewhere herein, but desirably the webbing is formed in such a way as to allow for ease of folding and conformation during delivery of the device near and past the heart's apical end. The rib (167) is a single one that forms a helical form when deployed. A schematic delivery wire or introducer (168) is shown.

Figure 6A:
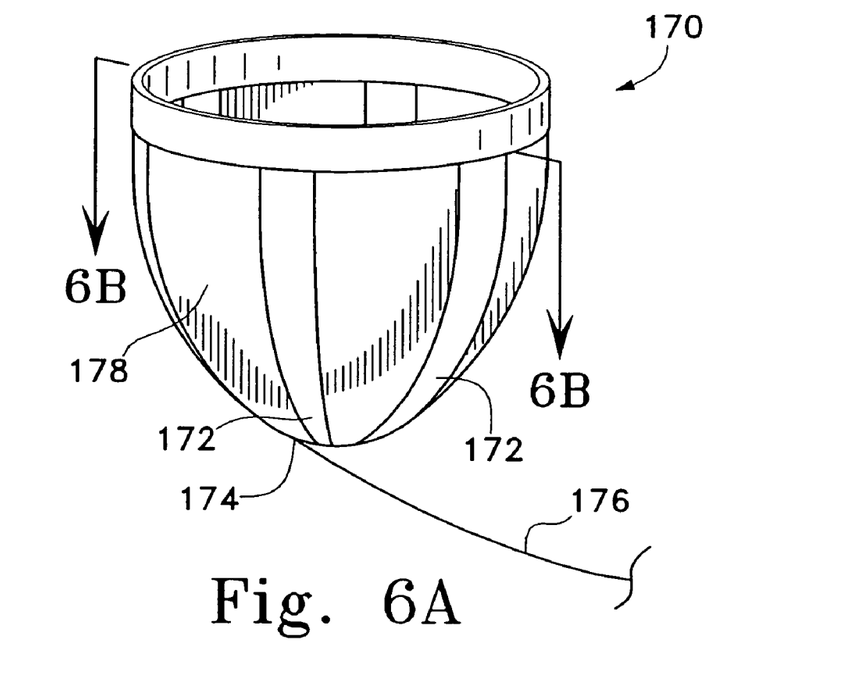
FIG. 6A shows a side view of the compliant member making up one variation of the invention.
Figure 6B:
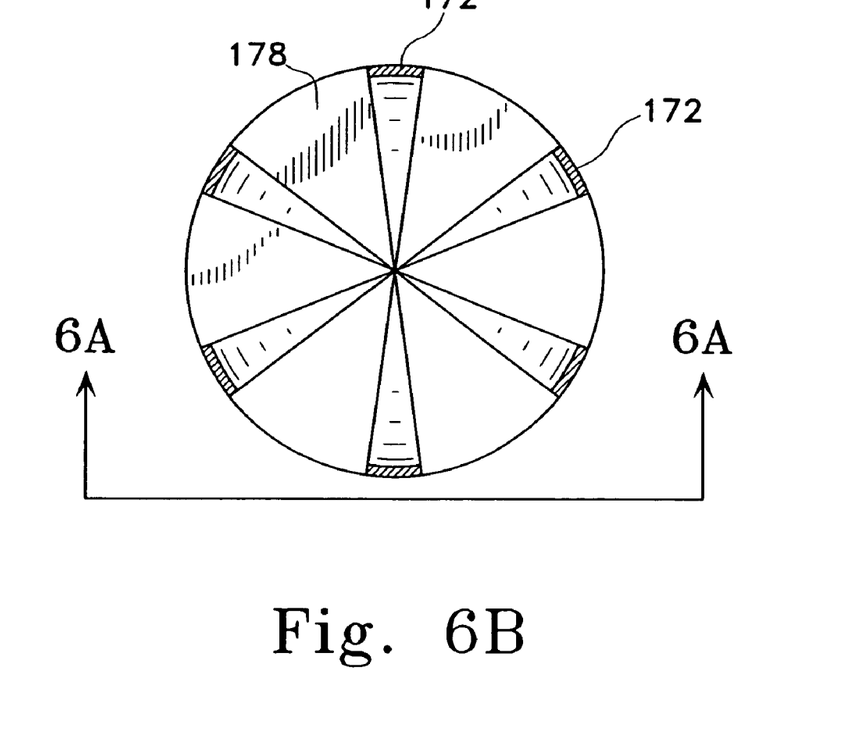
FIG. 6B shows a cross-sectional view of the FIG. 6A device.

FIGS. 6A and 6B show, respectively, a side view and a cross-sectional view of another ribbed variation (170). As was noted just above, the ribs (172) are not semi-circular in cross-section but have more of a flat aspect. In this variation, the ribs extend to an apical end (174). A schematic introducer (176) is shown. The ribs (172) may be separated by webbing (178) if desired.

Figures 7, 8, 9:
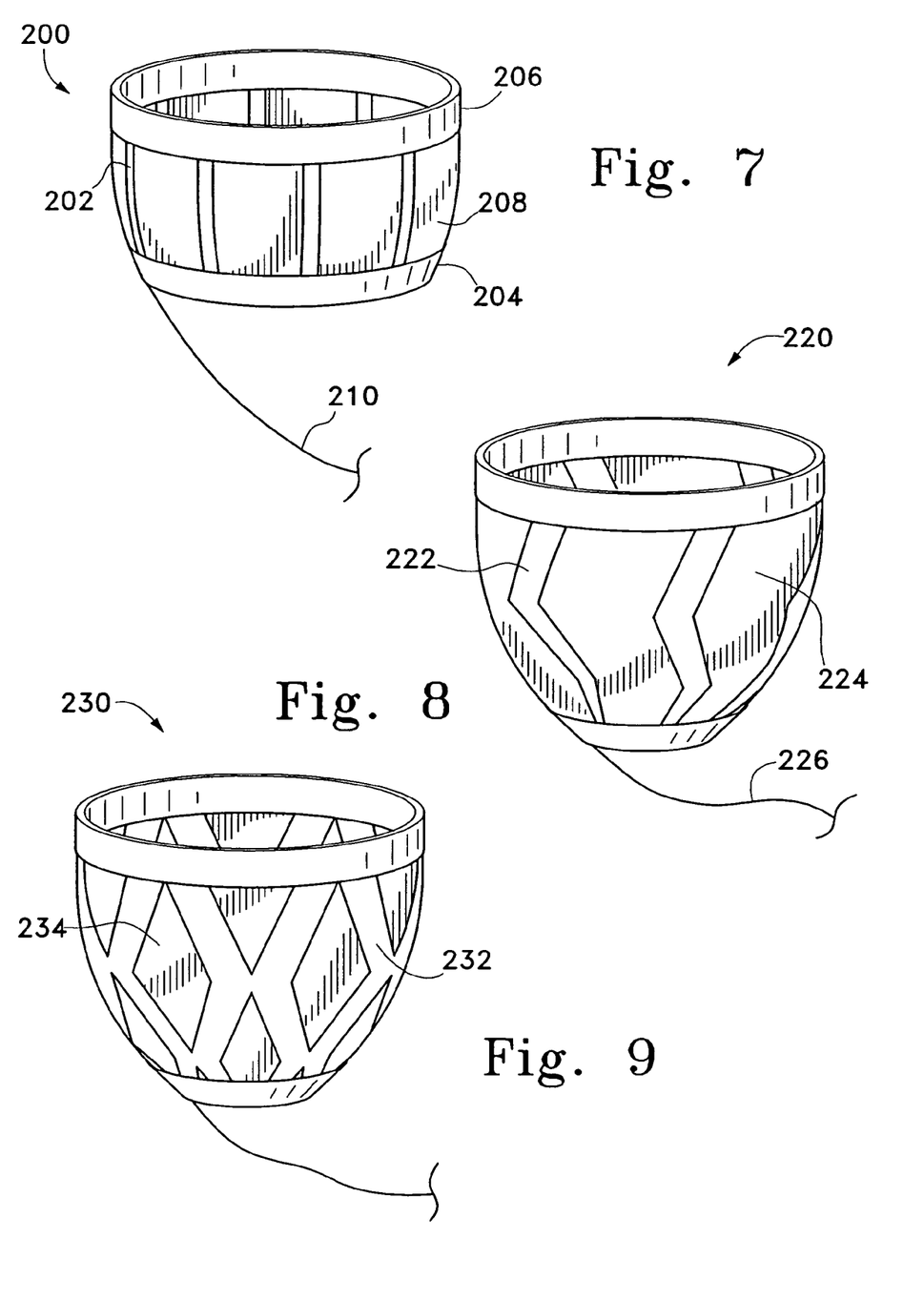
FIGS. 7, 8, and 9 show various side-views of variations of the invention.

FIG. 7 shows a side view of a variation (200) having ribs (202) that do not extend to the apical end, but instead stop at a lower band (204) and extend from an upper band (206). As was the case with the other variations of this type, the ribs may be separated by webbing (208). An introducer (210) is shown.

FIG. 8 shows a ribbed variation (220) of the inventive member in which the compliant member has ribs (222) that are zig-zag in shape. This rib variation minimizes the amount of material that is introduced as rib material but distributes the stiffer reinforcing material around the periphery of the devices quite nicely. The ribs (222), again, may be separated by webbing (224) material of the type discussed elsewhere. An introducer (226) is also shown. The ribs (232) are shown to be situated "in phase" but need not be. Other convoluted forms to the ribs, e.g., sine shaped ribs, U-shaped ribs, etc., are also within the scope of the invention.

FIG. 9 shows a side view of a variation (230) of the invention where the ribs (232) are joined at their respective apexes. The ribs (232) thereby form a continuous cage about the reinforcing member (230). The various spaces (234) remaining amongst the ribs (232) may be filled with ribbing (234) if so desired.

FIGS. 10A-10D show a number of variations of the "webbing" discussed above.

Figure 10A:
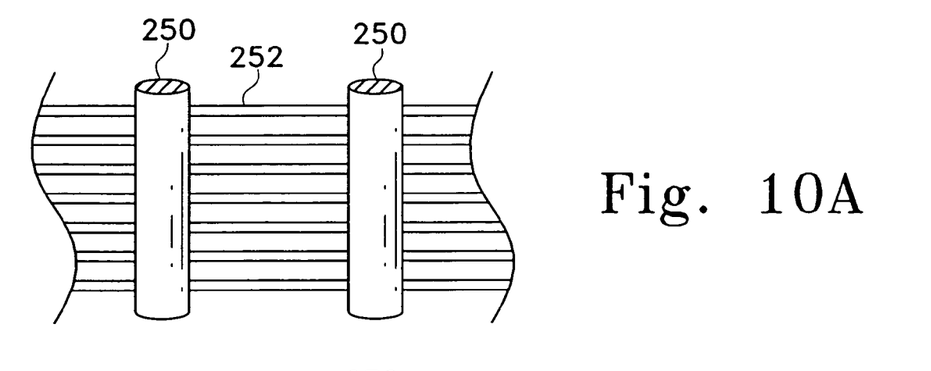
FIGS. 10A, 10B, 10C, and 10D show close-ups of various webbing variations suitable for the inventive device.

FIG. 10A shows a number of ribs (250) separated by and held together by strands (252) of an appropriate material. The strands (252) collectively making up the webbing may be single threads or collections of threads making up a cord-like assemblage.

Figure 10B:
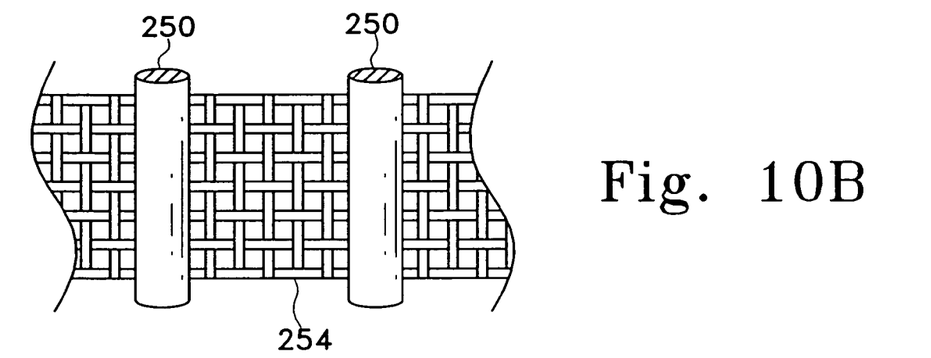

FIG. 10B shows the ribs (250) with a woven cloth (254) as the webbing material. The relative pic value may be in a range that extends between closed cloth to very open weave.

Figure 10C:
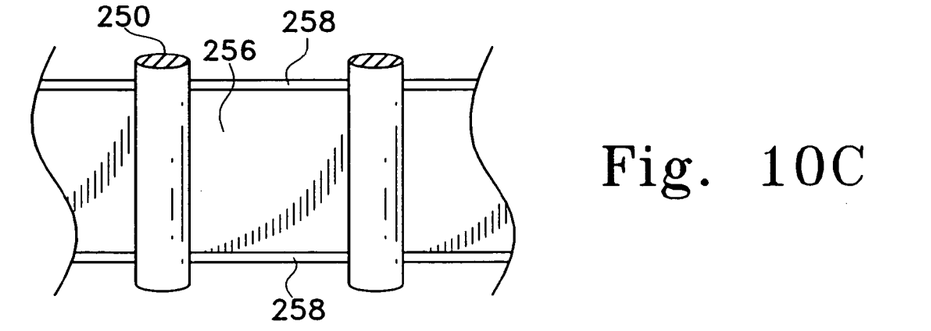

FIG. 10C shows the ribs (250) with a non-woven fabric (256) having optional upper and lower bands (258).

Figure 10D:
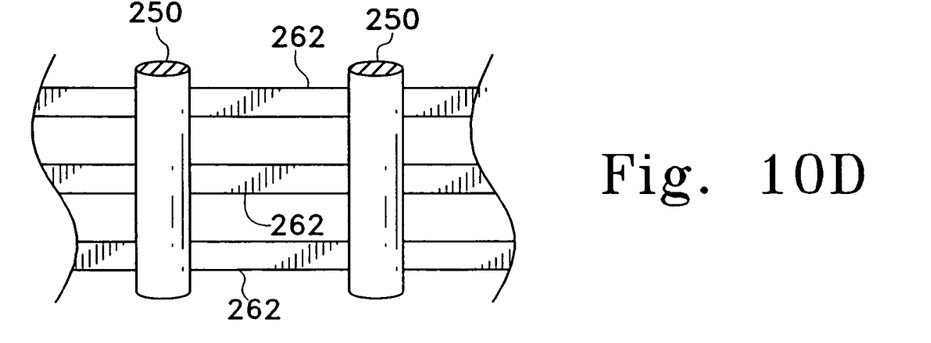

Finally, FIG. 10D shows ribs (250) separated by webbing (260) that is made up of a series of tapes (262) in turn formed from a fabric, woven or non-woven.

In addition to the generally pre-formed structures discussed above, we contemplate that such structures be formable within the pericardial sac as they are applied to the epicardium.

All of our variations are passive devices.

Figure 11A:
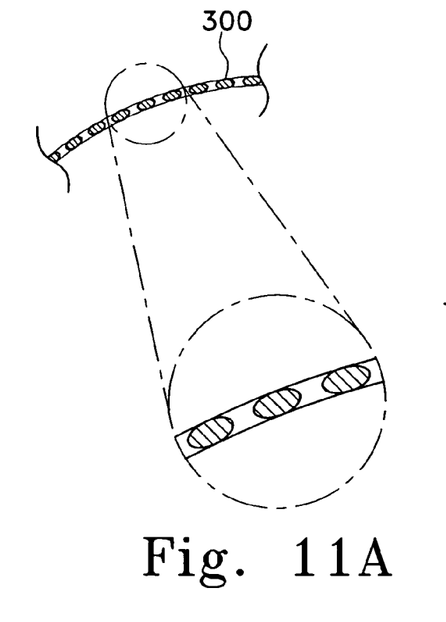
FIG. 11A shows a cross-sectional view of a flexible member having a non-adhering surface.

FIG. 11A depicts a cross-section of a flexible member (300) having an inner surface (302) that preferably does not adhere (or tends not to adhere) to the epicardium and also having an outer surface (304). In this variation of the invention, the inner surface (302) is coated with a material that tends not to form adhesions with the epicardium. The non-adhering material may be sprayed on or infused into another substrate having a differing proclivity for adhesion onto heart tissue.

Figure 11B:
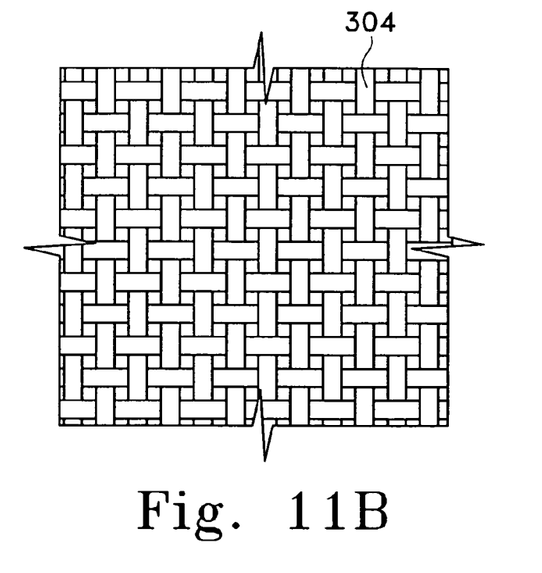
FIG. 11B shows a woven fabric, also a side view of the FIG. 11A fabric.

Incidentally, FIG. 11B show a typical woven fabric (304). The weave need not be as loose as is shown in FIG. 11B. It is also within the scope of this invention to use a random fabric or "non-woven" (as it is known in the polymer industry) A non-woven material (306) is shown in FIG. 12B in another variation of the invention for another purpose, but may be coated or used as a laminate member for the inventive device.

The material used that substantially prevents adhesion to the epicardium may be solid lubricious polymers such as polyfluorocarbons and polyolefins selected from the group consisting of polytetrafluoroethylene (PTFE or TFE), ethylene-chlorofluoroethylene (ECTFE), fluorinated ethylene propylene (FEP), polychlorotrifluoroethylene (PCTFE), polyvinylfluoride (PVF), polyvinylidenefluoride (PVDF), polyethylene (LDPE, LLDPE, and HDPE), and polypropylene. Other polymers such as the Nylons and polysulphones are also acceptable.

Again, these polymers may be applied in a variety of ways, e.g., as emulsions, dispersions, or solutions, to another substrate material as a covering or as an infusion or the substrate material may instead comprise the substantially non-adhering material.

Figure 12A:
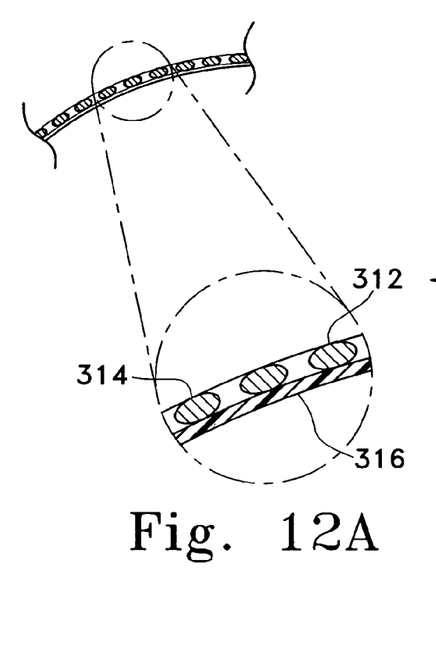
FIG. 12A shows a cross-sectional view of a flexible member having a composite non-adhering surface.
Figure 12B:
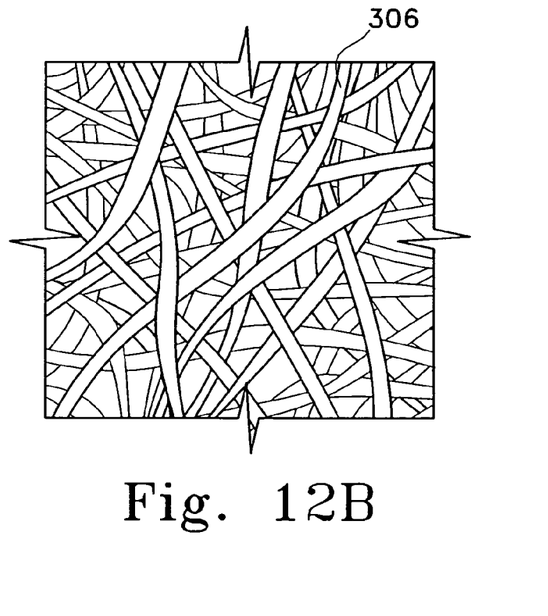
FIG. 12B shows a non-woven fabric, also a side view of the FIG. 12A fabric.

FIG. 12A shows a cross-section of variation (310) of the inventive device in which the inner surface (316) is a layer separate from the layer (318) adjacent the pericardium. The two layers (310) may be laminated together, if so desired. They need not be, since the function of the non-adhering side (316) is simply to prevent attachment of the epicardium to the inventive device. Again, both layers (314, 316) may be woven, non-woven, or a mixture as desired by the designer.

As is shown in FIG. 12A, the two surfaces (312, 316) may be independent structures, but may also be fixedly laminated together.

In addition to the webbed variations discussed here, the invention includes variations either not having webbing between the ribs or variations in which one or more ribs are introduced into the pericardial space and form a unitary structure once placed there. In particular, the non-webbed variations desirably include an adhesive which is specially adapted not to adhere to human tissue but specifically to adhere to itself and to certain selected polymers. Once such way of producing an aggregate whole would be to use the materials described in Published International Application WO-00/44287 owned by Prohold Medical Technologies, Inc. Such publication describes a modified cyanoacrylate polymer which, for instance, may be applied in its constituent parts in such a way that when the two constituent components are applied to different parts of, e.g., the introduced rib discussed elsewhere with regard to FIGS. 13A, 13B, 14, and 15, the device tends to stick to itself and form an integral or unified device when placed in certain ionic environments.

Figure 13A:
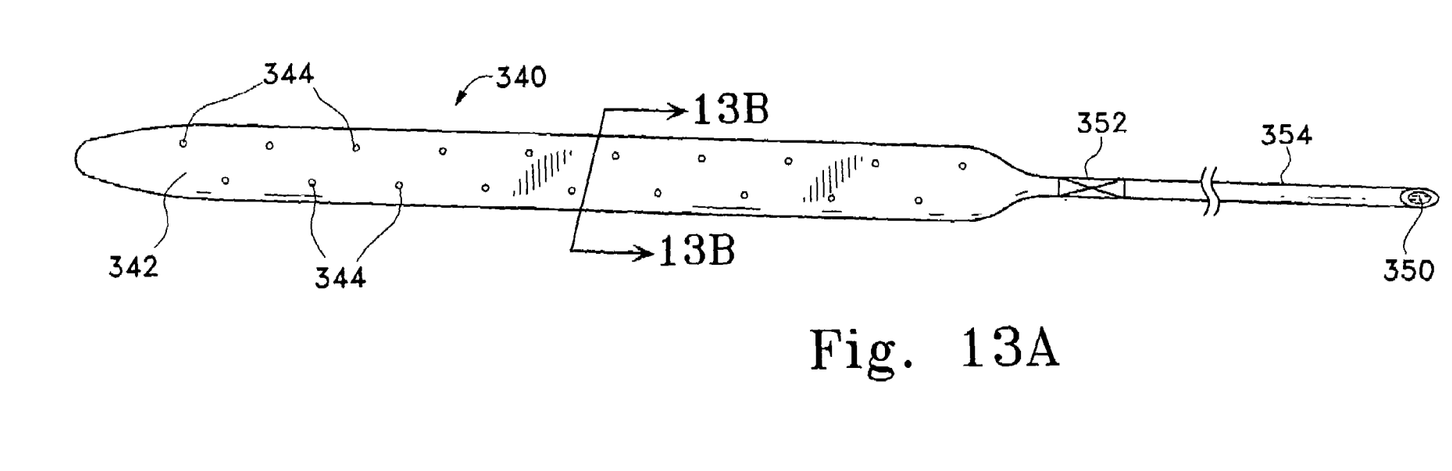
FIG. 13A shows a side view of a device that is introduced into the pericardial space as shown and forms a helix upon introduction.
Figure 13B:
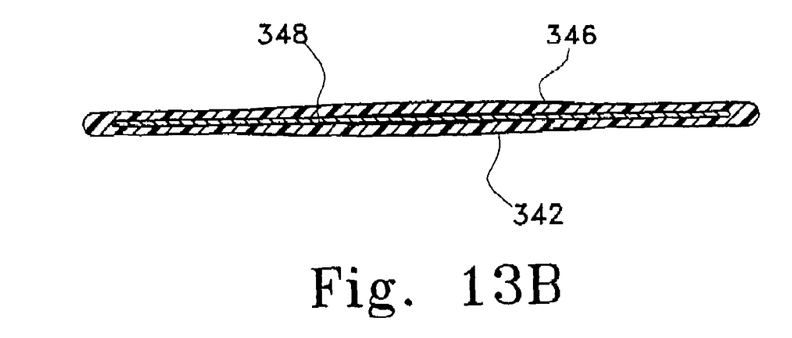
FIG. 13B shows a cross-section view of the FIG. 13A device.

In any case, FIGS. 13A and 13B show, respectively, a side view and a cross-sectional view of a device (340) which may be introduced into the pericardial space through a large catheter or through a cannula or the like. The device may be pre-formed so that as it is introduced into the pericardial space, it self-forms into a helical rib, much as was shown with respect to FIG. 5 above, but without the attached webbing. Preferably, the device (340) includes a first side (342) having a number of orifices (344) penetrating that side into an expandable lumen. The lumen opens upon introduction of some material into the region between the first side (342) and the opposing second side (346). A pre-formed and/or pre-formable stiffener (348) is shown, particularly in FIG. 13B. This pre-formed member aids in the curving formation of the device after introduction into the pericardial space.

Figure 15:
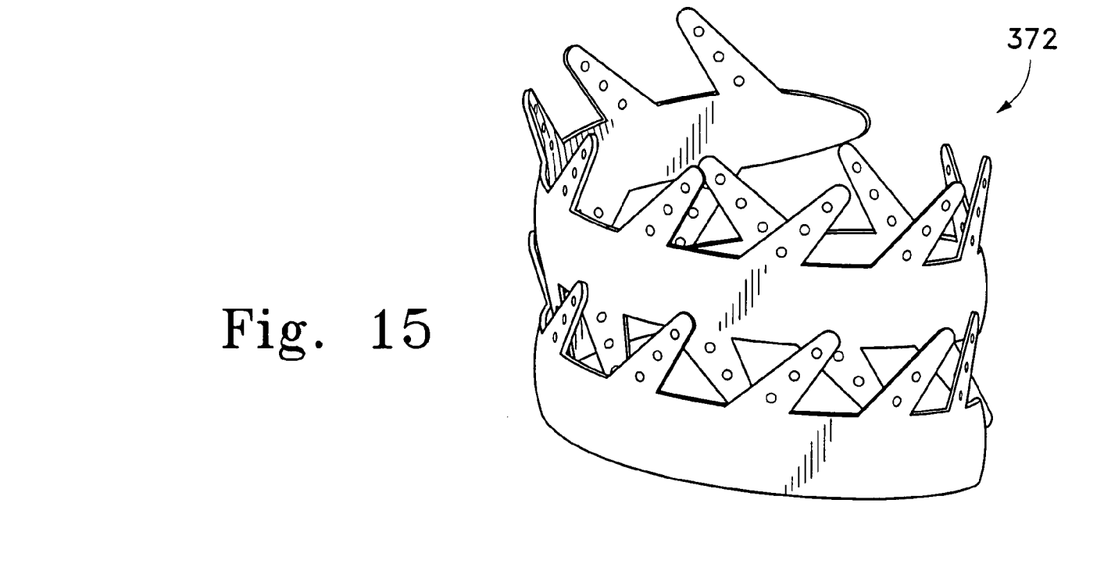
FIG. 15 shows a side view of the FIG. 14 device after introduction of the device and forming into a unitary support.

It is within the scope of this invention that the stiffener component (348) be removable after the device has been situated and glued or otherwise formed into an integral whole as is shown in FIG. 2 or 15. Further, the devices shown in FIG. 13A prior to being introduced into the space around the heart includes a lumen (350) for introducing a fluid into the interior of the device (340) and a joint (352) for separating the implant portion of the device (340) from the introducer section (354) that includes the delivery lumen (350).

Delivery lumen (350) may be used, for instance, for introducing one or more appropriate glues or adhesives into the device in such a way that it leaves or exudes through the various orifices (344), preferably in such a way that it sticks the sides of the device after it has been curled into an overlapping helix onto itself.

Figure 14:
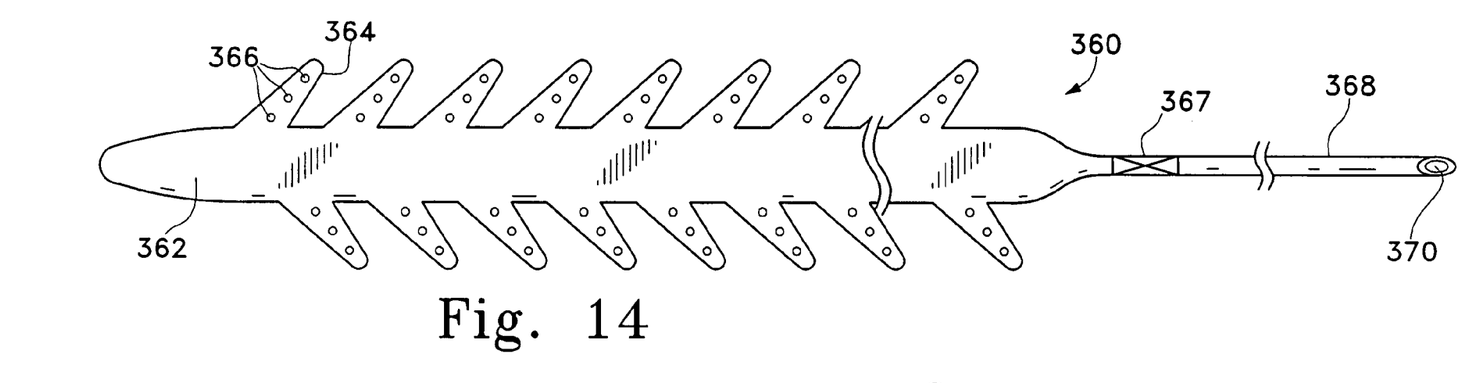
FIG. 14 shows a variation of the FIGS. 13A and 13B device.

FIG. 14 shows another variation of the inventive device (360) having a central rib section (362) and a number of ancillary ribs (364) having orifices (366), preferably on but one side of the device. The variation also includes separable joint (366) and introducer (368), preferably having a delivery lumen (370). Again, the body or central rib (362) preferably is pre-formed in such a way that, upon introduction into the pericardial space, the central rib (362) wraps about the heart in a helical fashion as it is physically introduced. The ancillary ribs (364) preferably would overlap in such a way as may be seen in FIG. 15 so that upon introduction of a glue or appropriate adhesive into the delivery lumen (370) and out of the orifices (366) that the overlapping ancillary ribs form an interlocking adhered together tubular assembly (372).

Obviously, the simpler device shown in FIGS. 13A and 13B also are formable into a glued-together helical rib, generally tubular member for contact with the epicardium. Again, as noted above, the devices once introduced into the pericardial space, should be placed in contact with the epicardium and allowed to form into an appropriate size and provide the appropriate amount of constraint or restraint of the appropriate cycle of the heartbeat.

This inventive device is neat and because it is situated in contact with the epicardium, is suitable for placement via any number of procedures, ranging from the most invasive—open chest surgery—to those that are much less invasive. A preferred procedure for placing the device is via a percutaneous approach potentially through the diaphragm beneath the xiphoid process. It is direct and uses short instruments for ease and accuracy. One highly desirable method for placement of the inventive reinforcement is shown in FIGS. 16A-16E.

Figure 16A:
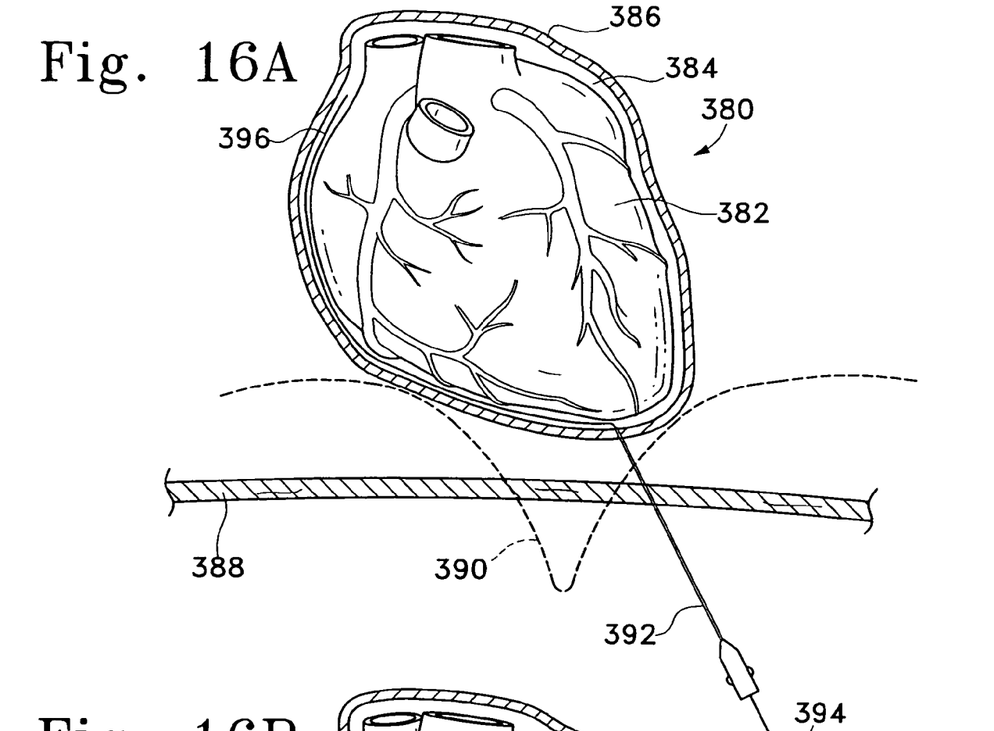
FIGS. 16A-16F show a method for introducing the inventive device into contact with the epicardium.

Shown in FIG. 16A is a heart (380) having an epicardial surface (382) surrounded by a pericardial space (384) holding pericardial fluid and all enclosed by the pericardium (386). The muscle sheet known as the diaphragm (388) may also be seen. For the purposes of depicting the spatial relationships in this procedure, the xiphoid process (510) is shown in shadow. All of the extraneous body parts not needed here for explanation of the procedure have been deleted for clarity.

Also shown in the first step of the procedure, is a needle (392). Much of the extraneous body structure not otherwise needed for explanation of the procedure have been omitted for clarity.

Also shown in FIG. 16A is the first step of the procedure. A suitably large hollow needle (392) and a guidewire (394) passing through the lumen of the needle (392) have been introduced below the xiphoid process (390) and through the diaphragm (388). The needle (392) and the guidewire (394) are shown having penetrated the pericardium (386). The distal end (396) of the guidewire (394) is shown passing up through the pericardial space to the upper end of the heart.

Figure 16B:
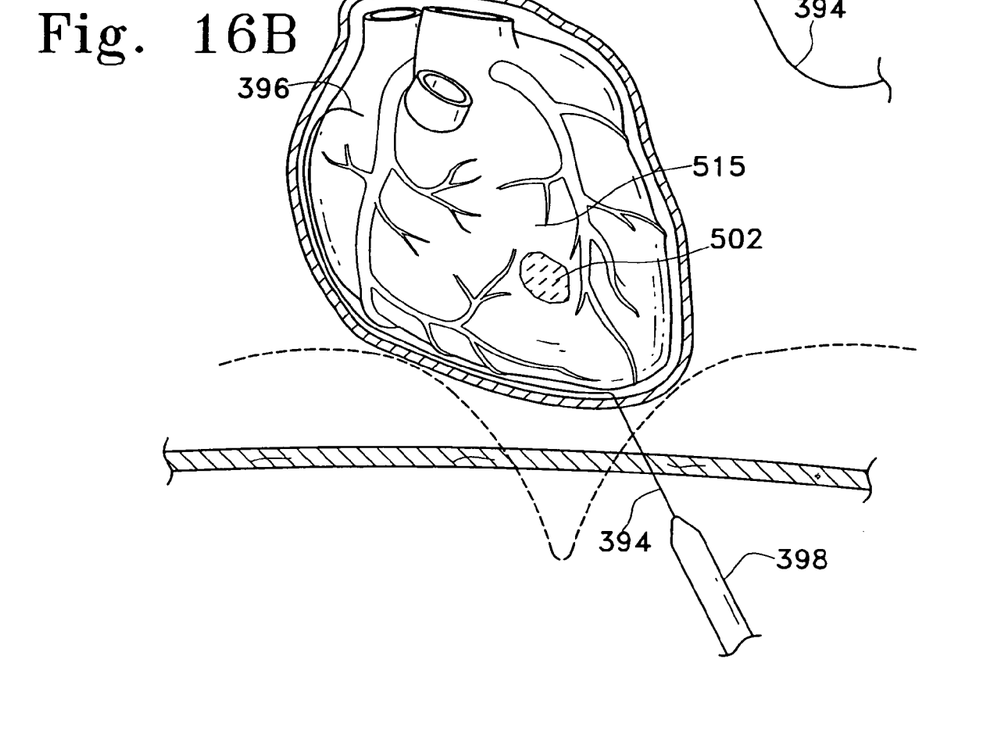

FIG. 16B shows that the needle has been removed from the guidewire (394) and the distal end (396) of the guidewire (394) has been manipulated to pass upwardly and across the epicardial surface of the heart. An introducer or cannula (398) is shown being passed up the guidewire (394).

Figure 16C:
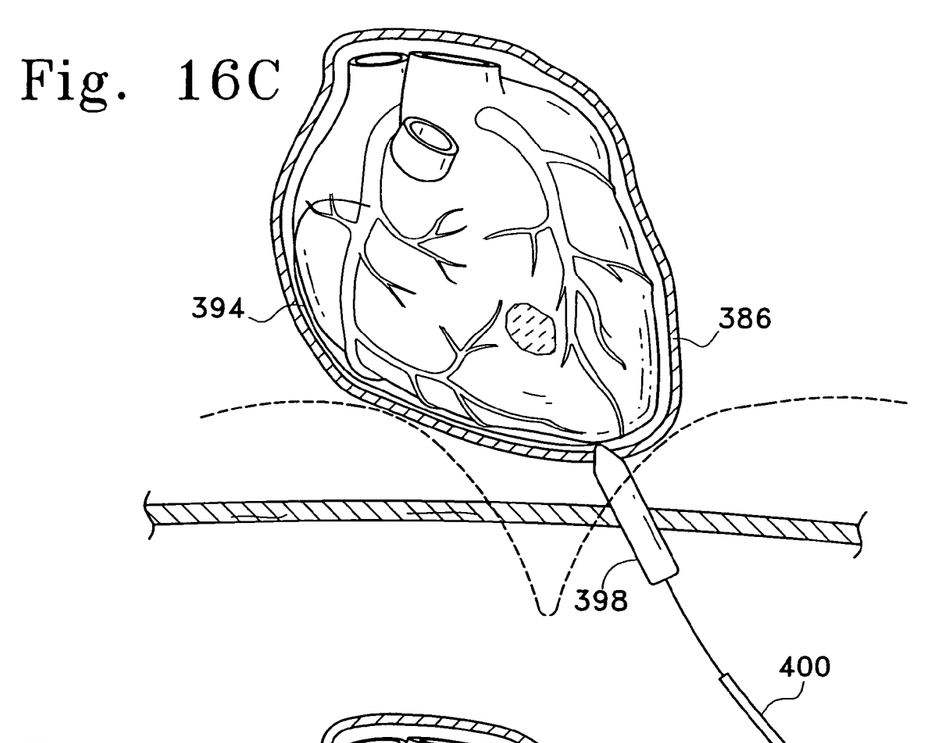

In FIG. 16C, the introducer or cannula (398) has been placed through the pericardium (386) and the delivery catheter (400) has been inserted and may be seen proceeding towards the proximal end of the introducer or cannula (398).

Figure 16D:
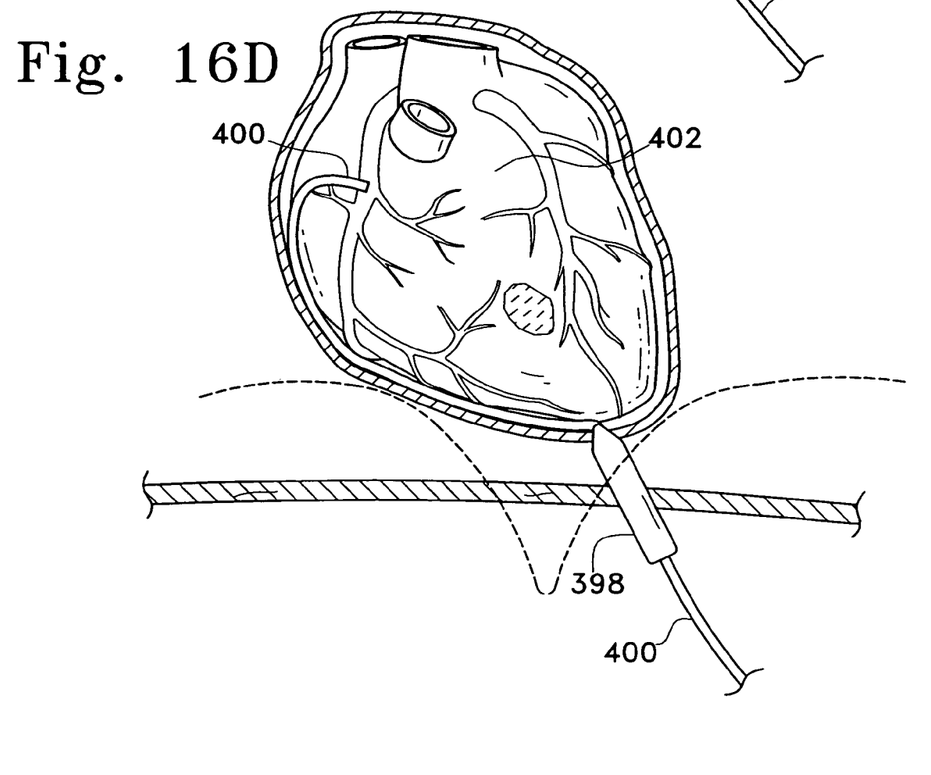

FIG. 16D shows the placement of the delivery catheter (400) prior to introduction of the inventive device with the catheter's distal end placed on an upper region of a ventricular wall needing support or constraint. One will note that the guidewire has been removed.

Figure 16E:
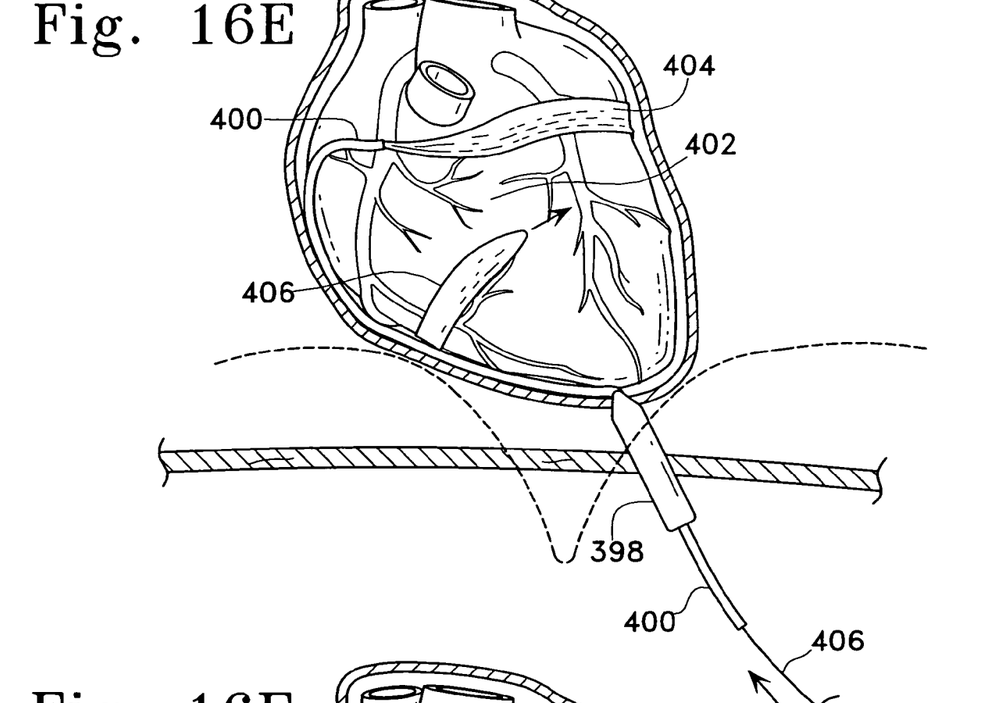

FIG. 16E shows the emergence of the inventive device (404) from the distal end of the catheter (400) and the beginning of the passage of the distal end (406) around the heart again.

Figure 16F:
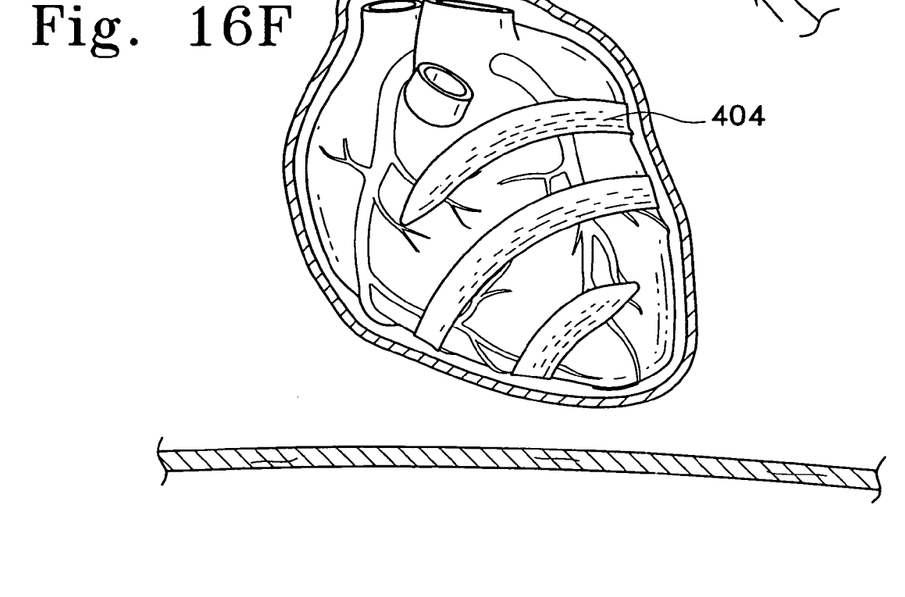

The inventive device (424) should follow the contours of the epicardium until it reaches its desired site as shown in FIG. 16F. A vibratory or oscillatory motion may be desirable to urge the device to its final spot.

In FIG. 16F, the catheter (400) and the introducer (398) have been removed and their access points repaired, leaving the device (404) against the epicardial surface for support.

Many alterations and modifications may be made by those of ordinary skill in this art, without departing from the spirit and scope of this invention. The illustrated embodiments have been shown only for purposes of clarity and the examples should not be taken as limiting the invention as defined in the following claims. Which claims are intended to include all equivalents, whether now or later devised.

What is claimed is:

1. A method for supporting an epicardium, said method comprising:

introducing an at least one generally elongate linear flexible element into a perleardial space through an access point so that the element advances along a helical path which encircles the heart as the element is introduced.

2. A method as in claim 1, wherein the flexible element is introduced through an access point below a xiphoid process through a peicardium wall into the pericardial space.

3. A method as in claim 2, further comprising the steps of puncturing skin beneath the xiphoid process with a needle and passing the needle and a guidewire through the pericardium into the pericardial space.

4. A method as in claim 3 further comprising the steps of withdrawing the needle and introducing an introducer over the guidewire through the pericardium into the pericardial space.

5. A method as in claim 3 further comprising the step passing a delivery catheter through the introducer over the guidewire through the pericardium into the pericardial space to a site adjacent an epicardium.

6. A method as in claim 5 wherein the elongate linear flexible element is introduced through the delivery catheter to the epicardium.

7. A method as in claim 1, wherein the at least one elongate linear flexible element comprises a ribbon-like member.

8. A method as in claim 7, wherein the at least one ribbon-like member has a width thickness ratio greater than about two.

9. A method as in claim 8, wherein the at least one ribbon-like member has a width thickness ratio greater than about seven.

10. A method as in claim 7, wherein the at least one ribbon-like member has a length and varies in flexibility along that length.

11. A method as in claim 7, wherein the at least one ribbon-like member has a length and varies in width along that length.

12. A method as in claim 7, wherein the at least one ribbon-like member has a length and varies in thickness along that length.

13. A method as in claim 7, wherein the at least one ribbon-like member is at least partially inflatable.

14. A method as in claim 13, wherein the at least one ribbon-like member is incrementally inflatable.

15. A method as in claim 7, comprising introducing multiple ribbon-like members.

16. A method as in claim 7, wherein the at least one ribbon-like member has a lumen extending from the proximal end at least partially to the distal end.

17. A method as in claim 7, wherein the at least one ribbon-like member includes at least one orifice, situated to open to other surfaces of the generally helical member when the support is helically configured.

18. A method as in claim 7, wherein the at least one ribbon-like member further comprising a source of glue or adhesive flowable through the at least one orifice, the glue or adhesive suitable for causing adherence only between portions of the generally helical member.

19. A method as in claim 18, wherein the glue or adhesive comprises a modified cyanoacrylate.

* * * * *